United States Patent [19]

Campbell et al.

[11] 4,128,571
[45] Dec. 5, 1978

[54] THERMAL CONVERSION OF 4-CYANO-SUBERONITRILE TO ACRYLONITRILE

[75] Inventors: Charles R. Campbell; William A. Heckle; Marion J. Mathews, all of Pensacola, Fla.

[73] Assignee: Monsanto Company, St. Louis, Mo.

[21] Appl. No.: 846,100

[22] Filed: Oct. 27, 1977

[51] Int. Cl.² .................. C07C 121/32; C07C 121/16
[52] U.S. Cl. ............................. 260/465.9; 260/465.1
[58] Field of Search ..................................... 260/465.9

[56] References Cited

U.S. PATENT DOCUMENTS

| 2,452,505 | 10/1948 | Teter | 260/465.9 |
| 2,671,107 | 3/1954 | Beckberger | 260/465.9 |
| 3,247,237 | 4/1966 | Hagemeyer, Jr. | 260/465.9 |
| 3,267,131 | 8/1966 | Campbell et al. | 260/465.9 |
| 3,280,168 | 10/1966 | Campbell et al. | 260/465.9 |

OTHER PUBLICATIONS

Arira et al., C.A., 72 (1970), 85681g.

*Primary Examiner*—Joseph Paul Brust
*Attorney, Agent, or Firm*—Thomas Y. Awalt, Jr.

[57] ABSTRACT

4-cyano-suberonitrile is continuously converted to acrylonitrile in a catalyst-free reaction at temperatures of about 700°–800° C.

7 Claims, No Drawings

THERMAL CONVERSION OF 4-CYANO-SUBERONITRILE TO ACRYLONITRILE

BACKGROUND OF THE INVENTION

A. Field of the Invention

The invention relates to the production of acrylonitrile from 4-cyano-suberonitrile.

B. The Prior Art

A long standing problem in the manufacture of adiponitrile from acrylonitrile by electrolytic dimerization has been the loss of adiponitrile by way of conversion to the by-products propionitrile and 4-cyano-suberonitrile, which, in a typical electrohydrodimerization reaction, occurs at a rate of about 8-14 mole % of the acrylonitrile employed at a starting material. Of this amount 4-7 mole % is attributable to losses involving conversion of acrylonitrile to the 4-cyano-suberonitrile.

Prior art efforts to recover these losses seem to have focused on the conversion of propionitrile to acrylonitrile; and little, if any attention was apparently given to recovery of acrylonitrile lost in the reactor through conversion to the 4-cyano-suberonitrile.

A reaction for converting the 4-cyano-suberonitrile to acrylonitrile at a commercially acceptable conversion and selectivity rate would be a significant advance in the art and is an object of this invention.

SUMMARY OF THE INVENTION 4-cyano-suberonitrile is continuously converted to acrylonitrile by passing the 4-cyano-suberonitrile in atomized form through an esentially oxygen and catalyst-free reaction zone at about 700°-800° C. at an hourly space velocity of about 2400-9300 and a linear velocity of 5-20 ft/sec (152.4-609.6 cm/sec). Within the above ranges, linear velocity and space velocity are adjusted in order to obtain, in relation to the selected temperature, the best conversion rate of 4-cyano-suberonitrile, without sacrifice of an acceptable selectivity rate of the acrylonitrile.

DETAILED DESCRIPTION OF THE INVENTION 4-cyano-suberonitrile may be employed as feedstock in the relatively impure form in which it is produced by electrohydrodimerization and recovered from the reactor by conventional distillation procedures. Providing it does not contain material deleterious to the reaction or the products, percent of purity is not critical. It is preferably diluted with an inert gas such as nitrogen, or a relatively inert noninterferring diluent such as steam. In order to prevent clogging of nozzles feeding the reactor it may be desirable to use propionitrile as a diluent. The feedstock, pure or diluted, is preferably atomized prior to or during the course of being fed into the reactor but it may be fed in liquid form into the reactor thereafter to be atomized.

We have discovered that thermal conversion of 4-cyano-suberonitrile at temperatures of 700°-800° C., preferably about 740°-800° C. will provide surprisingly higher conversions of the 4-cyano-suberonitrile and higher yields of the acrylonitrile than reactions otherwise similarily conducted at temperatures below about 700° C.

Reactions at such temperatures are conducted continuously at an hourly space velocity of 2400-9300, preferably 2600-8000. "Space velocity" is defined as the volume of gas per hour divided by the reactor volume.

Reactions at these temperatures are conducted at a linear velocity of 5-20 ft/sec (152.4-609.6 cm/sec) preferably 10-15 ft/sec (304.8-457.2 cm/sec) "linear velocity" is defined as the number of cubic units of gas per second divided by the cross sectional area of the reaction zone in square units. The length to diameter ratios of the reactor must be chosen so that the linear and space velocities will come within the requirements of the invention. The volume of 4-cyano-suberonitrile is calculated at the temperature and pressure prevailing in the reactor at operating conditions.

The following examples will serve further to illustrate the process of the invention.

EXAMPLES 1-25

4-cyano-suberonitrile (70.5 wt %) was introduced into a 10 foot (304.8 cm) by ¼ inch (7.62 cm) stainless steel (304) reactor having a 2 foot × ¼ inch stainless steel preheater section at temperatures of 650°-750° C. and at various linear velocities. A low mass radiant furnace was employed to maintain the reactor temperatures indicated. Feed rates, conditions and results are indicated on Table 1. Surprising increases in conversion rates are shown at temperatures above 700° C.

TABLE 1

| EXAMPLE | 1 | 2 | 3 | 4 | 5 | 6 | 7 |
|---|---|---|---|---|---|---|---|
| Reactor: Temperature | 750 | 750 | 750 | 750 | 750 | 750 | 750 |
| cc Void | 47.8 | 47.8 | 47.8 | 47.8 | 47.8 | 47.8 | 47.8 |
| Feed Rate: Liq. cc/hour | 240.9 | 240.9 | 508.5 | 250 | 392.1 | 273.7 | 428.6 |
| Liter N$_2$/hour | 2.0 | 2.0 | 3.5 | 2.0 | 3.5 | 3.5 | 3.5 |
| g/hour | | | | | | | |
| N$_2$ Feed Mole Ratio | 0.06 | 0.06 | 0.05 | 0.06 | 0.06 | 0.06 | 0.06 |
| Space Velocity: at Reactor Temp- -hr | 2632 | 2632 | 5828 | 2887 | 4557 | 3664 | 4956 |
| Liq. hourly-cc/hr/cc Cat | 5.04 | 5.04 | 10.6 | 5.23 | 8.21 | 5.73 | 8.97 |
| Contact Time - sec. | 1.37 | 1.37 | 0.62 | 1.25 | 0.79 | 1.10 | 0.72 |
| % Conversion to 4-cyano-suberonitrile | ** | 99.9 | ** | ** | ** | 98.8 | ** |
| Accountability (moles per 100 moles 4-cyano-suberonitrile converted) | 84.9 | ** | 84.8 | 87.3 | 75.0 | ** | 83.5 |
| Acrylonitrile | 30.9 | ** | 28.2 | 30.4 | 25.9 | ** | 28.6 |
| HCN | 3.4 | ** | 2.1 | 3.1 | 2.04 | ** | 2.4 |
| CH$_2$CN | 14.9 | ** | 10.8 | 14.8 | 9.7 | ** | 11.8 |
| Ethylene | 3.3 | ** | 2.7 | 4.5 | 4.4 | ** | 3.0 |
| Ethane | 0.3 | ** | 0.2 | 0.4 | 0.4 | ** | 0.4 |
| Methane | 0.8 | ** | 0.5 | 1.2 | 0.9 | ** | 0.5 |
| Propionitrile | 5.2 | ** | 4.8 | 4.8 | 3.8 | ** | 4.7 |
| AN/HCN Mole Ratio | 4.70 | ** | 6.72 | 5.0 | 6.5 | ** | 6.0 |
| Linear Vel., Ft/Sec. | 5.6 | 5.6 | 12.5 | 6.2 | 9.8 | 7.0 | 10.6 |
| Linear Vel., Cm/Sec. | 170.69 | 170.69 | 381 | 188.98 | 298.70 | 213.36 | 323.09 |

The feed make was as follows:
- 4-cyano-suberonitrile : 70 wt. %
- adiponitrile : 2.5 wt. %
- other materials : 27 wt. %

TABLE 1-continued

| EXAMPLE | 8 | 9* | 10* | 11* | 12* | 13* | 14* |
|---|---|---|---|---|---|---|---|
| Reactor: Temperature | 750 | 650 | 650 | 650 | 650 | 650 | 650 |
| cc Void | 47.8 | 47.8 | 47.8 | 47.8 | 47.8 | 47.8 | 47.8 |
| Feed Rate: Liq. cc/hour | 447.8 | 461.5 | 461.5 | 231.7 | 442.9 | 149.3 | 147.8 |
| Liter $N_2$/hour | 3.5 | 3.5 | 3.5 | 1.9 | 1.9 | 1.2 | 1.2 |
| g/hour | 467.4 | 481.8 | 481.8 | 241.8 | 253.6 | 155.8 | 154.3 |
| $N_2$ Feed Mole Ratio | 0.06 | 0.05 | 0.05 | 0.06 | 0.06 | 0.06 | 0.06 |
| Space Velocity: at Reactor Temp- -hr | 5165 | 4796 | 4796 | 2417 | 2528 | 1471 | 1541 |
| Liq. hourly-cc/hr/cc Cat | 9.37 | 9.66 | 9.66 | 4.85 | 5.08 | 3.12 | 3.09 |
| Contact Time - sec. | 0.70 | 0.75 | 0.75 | 1.48 | 1.42 | 2.45 | 2.34 |
| % Conversion to 4-cyano-suberonitrile | 95.8 | ** | 40.6 | ** | 49.6 | ** | ** |
| Accountability (moles per 100 moles 4-cyano-suberonitrile converted) | ** | 84.1 | ** | 94.0 | ** | 68.4 | 78.5 |
| Acrylonitrile | ** | 7.6 | ** | 12.6 | ** | 13.1 | 14.4 |
| HCN | ** | 0.4 | ** | 0.8 | ** | 0.8 | 0.8 |
| $CH_2CN$ | ** | 3.7 | ** | 5.8 | ** | 6.0 | 6.7 |
| Ethylene | ** | 0.2 | ** | 0.6 | ** | 0.8 | 1.2 |
| Ethane | ** | 0.02 | ** | 0.1 | ** | 0.1 | 0.2 |
| Methane | ** | 0.07 | ** | 0.2 | ** | 0.2 | 0.3 |
| Propionitrile | ** | 2.4 | ** | 3.4 | ** | 3.3 | 3.7 |
| AN/HCN Mole Ratio | ** | 9.9 | ** | 8.2 | ** | 8.6 | 8.8 |
| Linear Vel., Ft/Sec. | 11.1 | 10.3 | 10.3 | 5.2 | 5.4 | 3.2 | 3.3 |
| Linear Vel., Cm/Sec. | 338.33 | 313.94 | 313.94 | 158.39 | 164.59 | 97.53 | 100.58 |

| EXAMPLE | 15 | 16 | 17 | 18 | 19 | 20 | 21 |
|---|---|---|---|---|---|---|---|
| Reactor: Temperature | 650* | 700 | 700 | 700 | 700 | 700 | 700 |
| cc Void | 47.8 | 47.8 | 47.8 | 47.8 | 47.8 | 47.8 | 47.8 |
| Feed Rate: Liq. cc/hour | 147.4 | 363.6 | 397.4 | 309.8 | 288.5 | 219.8 | 225.6 |
| Liter $N_2$/hour | 1.2 | 3.6 | 3.6 | 2.4 | 2.4 | 1.7 | 1.7 |
| g/hour | 153.9 | 379.6 | 414.8 | 322.9 | 301.1 | 229.4 | 235.5 |
| $N_2$ Feed Mole Ratio | 0.06 | 0.07 | 0.07 | 0.05 | 0.06 | 0.06 | 0.05 |
| Space Velocity: at Reactor Temp- -hr | 1538 | 4046 | 4397 | 3679 | 3176 | 2410 | 2471 |
| Liq. hourly-cc/hr/cc Cat | 3.08 | 7.61 | 8.32 | 6.47 | 6.04 | 4.60 | 4.72 |
| Contact Time - sec. | 2.34 | 0.89 | 0.82 | 0.98 | 1.13 | 1.49 | 1.45 |
| % Conversion to 4-cyano-suberonitrile | 62.6 | ** | 68.3 | ** | 74.4 | ** | 81.9 |
| Accountability (moles per 100 moles 4-cyano-suberonitrile converted) | ** | 94.5 | ** | 80.5 | ** | 76.0 | ** |
| Acrylonitrile | ** | 21.1 | ** | 21.5 | ** | 23.0 | ** |
| HCN | ** | 1.4 | ** | 1.4 | ** | 1.6 | ** |
| $CH_2CN$ | ** | 9.0 | ** | 9.2 | ** | 10.1 | ** |
| Ethylene | ** | 1.9 | ** | 1.3 | ** | 1.5 | ** |
| Ethane | ** | 0.3 | ** | 0.2 | ** | 0.2 | ** |
| Methane | ** | 0.4 | ** | 0.3 | ** | 0.3 | ** |
| Propionitrile | ** | 4.5 | ** | 4.5 | ** | 4.6 | ** |
| AN/HCN Mole Ratio | ** | 7.5 | ** | 7.7 | ** | 7.1 | ** |
| Linear Vel., Ft/Sec. | 3.3 | 8.7 | 9.4 | 7.9 | 6.8 | 5.2 | 5.3 |
| Linear Vel., Cm/Sec. | 100.58 | 265.18 | 286.51 | 240.79 | 207.26 | 158.5 | 161.54 |

| EXAMPLE | 22 | 23 | 24 | 25 |
|---|---|---|---|---|
| Reactor: Temperature | 700 | 700 | 750 | 750 |
| cc Void | 47.8 | 47.8 | 47.8 | 47.8 |
| Feed Rate: Liq. cc/hour | 845.1 | 857.1 | 805.4 | 797.9 |
| Liter $N_2$/hour | 7.1 | 7.1 | 6.7 | 6.7 |
| g/hour | 882.2 | 894.8 | 840.7 | 832.9 |
| $N_2$ Feed Mole Ratio | 0.06 | 0.06 | 0.06 | 0.06 |
| Space Velocity: at Reactor Temp- -hr | 9309 | 9434 | 9327 | 9240 |
| Liq.hourly-cc/hr/cc Cat | 17.7 | 17.9 | 16.9 | 16.7 |
| Contact Time - sec. | 0.39 | 0.38 | 0.39 | 0.39 |
| % Conversion to 4-cyano-suberonitrile | ** | 41.8 | ** | 90.4 |
| Accountability (moles per 100 moles 4-cyano-suberonitrile converted) | 92.2 | ** | 73.7 | ** |
| Acrylonitrile | 12.6 | ** | 22.1 | ** |
| HCN | 0.7 | ** | 1.5 | ** |
| $CH_2CN$ | 5.4 | ** | 9.0 | ** |
| Ethylene | 0.9 | ** | 1.9 | ** |
| Ethane | 0.2 | ** | 0.2 | ** |
| Methane | 0.1 | ** | 0.4 | ** |
| Propionitrile | 3.0 | ** | 4.1 | ** |
| AN/HCN Mole Ratio | 8.9 | ** | 7.5 | ** |
| Linear Vel., Ft/Sec. | 20.0 | 20.2 | 20.0 | 19.8 |
| Linear Vel., Cm/Sec. | 609.6 | 615.7 | 609.6 | 603.5 |

*Comparison examples
**Conversion measurements and acountability and analysis measurements were made alternately due to limited quantities available.

EXAMPLE 26

A mixture of 50 weight % propionitrile and 50 weight % of the feed of examples 1-25 was fed into the same reactor as described above. The temperature employed was 750° C. and the mole ratio of nitrogen to the mixture of propionitrile and the feed make described above was 0.06. Residence time was 1.06 second and the run continued for 53 minutes. The conversion of propionitrile was 52% and that of the 70% 4-cyano-suberonitrile was 96%. Production of acrylonitrile in the amount of 25 grams of acrylonitrile per 100 grams of the feed mixture was obtained.

EXAMPLE 27

A feed mix consisting of two parts by weight of propionitrile and one part by weight of the 4-cyano-suberonitrile (70 weight %) feed make of examples 1-25 was fed into the same 10 foot reactor. The temperature was maintained at 750° and the mole ratio of nitrogen to the feed mixture was 0.06. 63% of the propionitrile and 99% of the 4-cyano-suberonitrile was converted; and 25 pounds of acrylonitrile per 100 pounds of the feed make was obtained.

We claim:

1. A continuous process for producing acrylonitrile from 4-cyano-suberonitrile comprising passing 4-cyano-suberonitrile in atomized form through an essentially oxygen and catalyst-free reaction zone at a temperature of about 700°–800° C., an hourly space velocity of 2400–9300 and a linear velocity of 5–20 ft/sec.

2. The continuous process of claim 1 wherein the catalyst free reaction zone is maintained at a temperature of 740°–800° C.

3. The continuous process of claim 1 wherein the reaction zone is maintained at a temperature of about 750° C.

4. The continuous process of claim 1 wherein the hourly space velocity is about 2600–8000.

5. The continuous process of claim 1 wherein the linear velocity is about 10–15 ft/sec.

6. The continuous process of claim 1 wherein the catalyst-free reaction zone is maintained at a temperature of about 750° C., the hourly space velocity is about 2600–8000, and the linear velocity is about 10–15 ft/sec.

7. The continuous process of claim 1 wherein the 4-cyano-suberonitrile is diluted with propionitrile before being converted to acrylonitrile.

* * * * *